United States Patent [19]
Speyer et al.

[11] Patent Number: 5,744,455
[45] Date of Patent: Apr. 28, 1998

[54] REDUCTION OF ANTHRACYCLINE-INDUCED CARDIOTOXICITY

[75] Inventors: James Leonard Speyer, New York, N.Y.; Franco Mario Muggia, Los Angeles, Calif.; Michael David Green, North Carlton, Australia

[73] Assignee: New York University, New York, N.Y.

[21] Appl. No.: 116,399

[22] Filed: Sep. 3, 1993

Related U.S. Application Data

[63] Continuation of Ser. No. 860,581, Mar. 27, 1992, Pat. No. 5,242,901, which is a continuation of Ser. No. 702,741, Apr. 15, 1993, abandoned, which is a continuation of Ser. No. 579,174, Sep. 5, 1990, abandoned, which is a continuation of Ser. No. 149,114, Jan. 27, 1988, abandoned.

[51] Int. Cl.$^6$ .......................... A61K 31/495; A61K 31/70
[52] U.S. Cl. .......................... 514/34; 514/255; 514/908; 514/974
[58] Field of Search .................. 514/8, 255, 34, 514/908, 974; 536/64

[56] References Cited

U.S. PATENT DOCUMENTS

| | | | |
|---|---|---|---|
| 4,275,063 | 6/1981 | Creighton | 424/250 |
| 4,755,619 | 7/1988 | Creighton et al. | 560/123 |
| 4,764,614 | 8/1988 | Miller | 544/357 |
| 4,963,551 | 10/1990 | Palepu et al. | 514/252 |
| 4,963,679 | 10/1990 | Tu et al. | 544/357 |
| 5,242,901 | 9/1993 | Speyer et al. | 536/64 |

OTHER PUBLICATIONS

Doroshow JH, Locker GY, Myers CE: Enzymatic defenses of the mouse heart against reactive oxygen metabolites. *J. Clin. Invest.* 1980;65:129–135.

Olson RD, Boerth RC, Gerber JG, Nies AS: Mechanism of Adriamycin cardiotoxicity: evidence for oxidative stress. *Life Sciences* 1981;29:1393–1401.

Doroshow JH: Effect of anthracycline antibiotics on oxygen radical formulation in rat heart. *Cancer Research* 1983;43:460–472.

Gutteridge JMC: Lipid peroxidation and possible hydroxyl radical formation stimulated by the self-reduction of a doxorubicin–iron(III) complex. *Biochem. Phar.* 1984;33(11):1725–1728.

Bristow MR, Sageman WS, Scott RH, Billingham ME, Bowden RE, Kernoff RS, Snidow GH, Daniels JR: Acute and chronic cardiovascular effects of doxorubicin in the dog: the cardiovascular pharmacology of drug–induced histamine release. *JCP* 1980;2:487–515.

Bristow MR, Minobe WA, Billingham ME, Marmor JB, Johnson GA, Ishimoto BM, Sageman WS, Daniels JR: Anthracycline–associated cardiac and renal damage in rabbits. *Lab. Invest.* 1981;45(2):157162, 157164.

Decorti G, Klugmann FB, Candussio L, Basa M, Mallardi F, Grill V, Baldini L: Effect of polyethylene glycol 400 on Adriamycin induced histamine release. *Eur. J. Cancer Clin. OncoL* 1986;22(7):793–799.

Klugmann FB, Decorti G, Candussio L, Grill V, Mallardi F, Baldini L: Inhibitors of Adriamycin–induced histamine release in vitro limit Adriamycin cardiotoxicity in vivo. *Br. J. Cancer* 1986;54:743–748.

(List continued on next page.)

Primary Examiner—Jeffrey E. Russel
Attorney, Agent, or Firm—Darby & Darby

[57] ABSTRACT

Disclosed is a method for preventing cardiotoxicity in a human in need of such preventive treatment, the method including administering an effective amount of a bisdioxopiperazine. Also disclosed is a method for preventing cardiotoxicity induced by the administration of an anthracycline. Further, a tumoricidal, cardioprotective combination of agents is disclosed.

8 Claims, 3 Drawing Sheets

OTHER PUBLICATIONS

Decorti G, Klugmann FB, Candussio L, Baldini L: Characterization of histamine secretion induced by anthracyclines in rat peritoneal mast cells. *Biochem. Pharm.* 1986;35(12):1939–1942.

Olson HM, Young DM, Prieur DJ, LeRoy AF, Reagan RL: Electrolyte and morphologic alterations of myocardium in adriamycin-treated rabbits. *Amer. J. Pathol.* 1974;77:439–454.

Zorzato F, Saiviati G, Facchinetti T, Volpe P: Doxorubicin induces calcium release from terminal cisternae of skeletal muscle: a study on isolated sarcoplasmic reticulum and chemically skinned fibers. *J. Biol. Chem.* 1985;260(12):7349–7355.

Caroni P, Villani F, Carafoli E: The cardiotoxic antibiotic doxorubicin inhibits the $Na^+/Ca^{2+}$ exchange of dog heart sarcolemmal vesicles. *Elsevier* 1981;130(2):184–188.

Anghileri LJ: $Ca^{2+}$-Transport inhibition by the antitumor agents Adriamycin and daunomycin. *Arzneim.–Forsch./Drug Res.* 1977;27(1),6:1177–1180.

Boucek RJ, Olson RD, Brenner DE, Ogunbunmi EM, Inui M, Fleischer S: The major metabolite of doxorubicin is a potent inhibitor of membrane–associated ion pumps: a correlative study of cardiac muscle with isolated membrane fractions. *J. Biol. Chem.* 1987;262(33):15851–15856.

Tomlinson CW, Godin DV, Rabkin SW: Adriamycin cardiomyopathy: implications of cellular changes in a canine model with mild impairment of left ventricular function. *Biochem. Pharm.* 1985;34(22):4033–4041.

Iwamoto Y, Hansen IL, Porter TH, et al: Inhibition of coenzyme $Q_{10}$-enzymes, succinoxidase and NADH–oxidase, by Adriamycin and other quinones having antitumor activity. *Biochem. Biophys. Res. Commun.* 1974;58:633–638.

Bertazzoli C, Ghione M: Adriamycin associated cardiotoxicity: research on prevention with coenzyme Q. *Pharm. Res. Comm.* 1977;9(3):235–244.

Zbinden G, Bachmann E, Bolliger H: Study of coenzyme Q in toxicity of Adriamycin. 1977 Elsevier/North–Holland Biomedical Press, p. 219.

Combs AB, Acosta D, Folkers K: Prevention by coenzyme $Q_{10}$ of the cardiotoxicity of Adriamycin in cultured heart cells. *IRCS Med. Sci.* 1976;4:403.

Rosenoff SH, Brooks E, Bostick F, Young RC: Alterations in DNA synthesis in cardiac tissue induced by Adriamycin in vivo–Relationship to fatal toxicity. *Biochem. Pharm.* 1971;24:18981901.

Arena E, D'Alessandro N, Dusonchet L, Gebbia N, Gerbasi F, Sanguedolce R, Rausa L: Influence of pharmacokinetic variations on the pharmacological properties of Adriamycin. (*Univ. Palermo*). (Not dated).

Torti FM, Bristow MR, Howes AE, Aston D, Stockdale FE, Carter SK, Kohler M, Brown BW, Billingham ME: Reduced cardiotoxicity of doxorubicin delivered on a weekly schedule. *Ann. Intern. Med.* 1983;99(6):745–749.

Legha SS, Benjamin RS, Mackay B, et al: Reduction of doxorubicin cardiotoxicity by prolonged continuous intravenous infusion. *Ann. Intern. Med.* 1982;96:133–139.

Weiss AJ, Metter GE, Fletcher WS, Wilson WL, Grage TB, Ramirez G: Studies on Adriamycin using a weekly regimen demonstrating its clinical effectiveness and lack of cardiac toxicity. *Cancer Treat. Rep.* 1976;60:813–822.

Weiss AJ, Manthel RW: Experience with the use of Adriamycin in combination with other anticancer agents using a weekly schedule, with particular reference to lack of cardiac toxicity. *Cancer* 1977;40:2046–52.

Byfield JE, Seagren S, Chan PYM: Adriamycin (AD) cardiotoxicity (CT): clues to mitigation. *ASCO Abstracts* 1977;Mar.:275.

Nagineni CN, Yamada T, Yang JJ, Seraydarian MW: Effects of Adriamycin on enzymes of adenine nucleotide metabolism in heart cell cultures. *Res. Commun. Chem. Path. Pharm.* 1985;50(2):301305.

Pelikan PCD, Weisfeldt ML, Jacobus WE, Miceli MV, Bulkley BH, Gerstenblith G: Acute doxorubicin cardiotoxicity: functional, metabolic, and morphologic alterations in the isolated, perfused rat heart. *J. Cardiovasc. Pharm.* 1986;8:1058–1066.

Gibbs CL: Acute energetic effects of daunomycin on rabbit heart muscle. *J. Cardiovasc. Pharm.* 1985;7:556–561.

Seraydarian MW, Artaza L: Modification by adenosine of the effect of Adriamycin on myocardial cells in culture. *Cancer Research* 1979;39:2940–2944.

Saman S, Jacobs P, Opie LH: Mechanism of acute anthracycline cardiotoxicity in isolated rat hearts: Carminomycin versus Daunomycin. *Cancer Research* 1984;44:1316–1320.

Villani F, Piccinini F, Merelli P, Favalli L: Influence of Adriamycin of calcium exchangeability in cardiac muscle and its modification by ouabain. *Chemical Pharm.* 1977;27:985–987.

DiMarco A, Dasdia T, Pastori W: Interaction of calcium ions and cAMP on the cytotoxic effect of doxorubicin. *Tumori* 1984;70:217–221.

Singal PK, Panagia V: Direct effects of Adriamycin on the rat heart sarcolemma. *Res. Commun. Chem. Path. Pharm.* 1984;43(1):67–72.

Lazarus ML, Rossner KL, Anderson KM: Adriamycin–induced alterations of the action potential in rat papillary muscle. *Cardiovasc. Res.* 1980;14:446–450.

Azuma J, Serelakis N, Hasegawa H, et al: Adriamycin cardiotoxicity: possible pathogenic mechanisms. *J. Mol. Cell. Cardiol.* 1981;13:381–397.

Mhatre R, Herman E, Huidobro A, Waravdekar V: The possible relationship between metabolism and cardiac toxicity of daunomycin and related compounds. *J. Pharm. Exp. Ther.* 1971;178:216–222.

Wheeler DMS: Another hypothesis concerning the antitumor activity and cardiotoxicity of daunorubicin (NSC–82151) and Adriamycin (NSC–1 23127). *Cancer Chemother. Reports, Part 1* 1975;59(2):258259.

Levey GS, Levey BA, Ruiz E, Lehotay DC: Selective inhibition of rat and human cardiac guanylate cyclase in vitro by doxorubicin (Adriamycin): a possible link to anthracycline cardiotoxicity. *Cardiol.* 1979;1 1:591–599.

Lehotay DC, Levey BA, Rogerson BJ, Levey GS: Inhibition of cardiac guanylate cyclase by doxorubicin and some of its analogs: possible relationship to cardiotoxicity. *Cancer Treat. Reports* 1982;66(2):311–316.

Law J, Fumagalli A, Schein PS, Rahman A: Selective inhibition of cardiac cyclic nucleotide phosphodiesterases by doxorubicin and daunorubicin. *Life Sciences* 1985;36:589–599.

Fiallo MML, Garnier–Suillerot A: Interaction of Adriamycin with cardiolipin–containing vesicles: evidence of an embedded site for the dihydroanthraquinone moiety. *Biochem. et Biophys. Acta* 1986;854:143–146.

Siegfried JA, Kennedy KA, Sartorelli AC, Tritton TR: The role of membranes in the mechanism of action of the antineoplastic agent Adriamycin: spin–labeling studies with chronically hypotoxic and drugresistant tumor cells. *J. Biol. Chem.* 1983;258(1):339–343.

Nicolay K, van der Neut R, Folk JJ, de Kruijff B: Effects of Adriamycin on lipid polymorphism in cardiolipin–containing model and mitochondrial membranes. *Biochem. et Bioshys. Acta* 1985;819:5565.

Tritton TR, Yee G: The anticancer agent Adriamycin can be actively cytotoxic without entering cells. *Science* 1982;217:248–249.

Lewis W, Kleinerman J, Puszkin S: Interaction of Adriamycin in vitro with cardiac myofibrillar proteins. *Circulation* 1982, 50:547–553.

Ito H, Miller SC, Billingham ME, Akimoto H, Torti SB, Wade R, Gahimann R, Lyons G, Kedes L, Torti FM: Doxorubicin selectively inhibits muscle gene expression in cardiac muscle cells in vivo and in vitro. *Proc. Natl. Acad. Sci. USA* 1990;87:4275–4279.

Zahringer J, Hofling B: Adriamycin–cardiomyopathy: changes in myocardial polyribosomes and mRNA levels. In: *Myocardial Biopsy: Diagnostic Significance*, ed. by Bolte HD. Springer Verlag: Berlin, 1980.

Myers CE, McGuire WP, Liss RH, Ifrim I, Grotzinger K, Young RC: Adriamycin: the role of lipid peroxidation in cardiac toxicity and tumor response. *Science* 1977;Jul.:165–167.

Myers CE, McGuire WP, Young RC: Adriamycin: amelioration of toxicity by a–tocopherol. *Cancer Treatment Reports* 1976;60(7):961962.

Doroshow JH, Locker GY, Ifrim I, Myers CE: Prevention of Doxorubicin cardiac toxicity in the mouse by N–acetylcysteine. *J. of Clin. Invest.* 1981;68(Oct.):1053–1064.

Bristow MR, Sageman WS, Scott RH, Billingham ME, Bowden RE, Kernoff RS, Snidow GH, Daniels JR: Acute and chronic cardiovascular effects of doxorubicin in the dog: the cardiovascular pharmacology of drug–induced histamine release. *JCP* 1980;2:487–515.

Kantrowitz NE, Bristow MR, Harrison WD, Minobe WA, Sageman WS, Billingham ME: Mediation of subacute anthracycline cardiotoxicity in rabbits by cardiac histamine release. *JCP* 1983;5:913–919.

Klugmann FB, Decorti G, Candussio L, Grill V, Mallardi F, Baldini L, Zweyer M: Amelioration of r'–epidoxorubicin–induced cardiotoxicity by sodium cromoglycate. *Eur. J. Cancer Clin. Oncol.* 1989;25(2):361–368.

Daniels JR, Billingham ME, Gelbart A, Bristow MR: Effect of verapamil and propranolol on Adriamycin–induced cardiomyopathy in *rabbits*. *Circulation* 1976;54:11–20.

Milei J, Vazquez A, Boveris A, Llesu Y S, Molina HA, Storino R, Marantz A: The role of prenylamine in the prevention of adriamycininduced cardiotoxicity: a review of experimental and clinical findings. *J. Int. Med. Res.* 1988;16(1):19–30.

Okada R, Kasuya H, ih S, Ogawa M: Histopathological study of Adriamycin (ADR)–Cardiotoxicity in rats and the protective effects of 9–blockade, Ca–antagonist and COQ10. *Jap. Circ. J.* 1983;47:845.

Bertazzoli C, Sala L, Solica E, Ghione M: Experimental Adriamycin cardiotoxicity prevented by ubiquinone in vivo in rabbits. *IRCS Med Sci.* 1975;3:468.

Bertazzoli C, Ghione M: Adriamycin associated cardiotoxicity: research on prevention with coenzyme $Q_{10}$. *Pharm. Res. Comm.* 1977;9(3):235–243.

Combs AB, Choe JY, Truong DH, Folkers K: Reduction by coenzyme $Q_{10}$ of the acute toxicity of Adriamycin in mice. *Res. Comm. Chem. Path. & Pharm.* 1977;18(3):565–571.

Ohhara H, Kanaide H, Nakamura M: A protective effect of coenzyme $Q_{10}$ on the Adriamycin–induced cardiotoxicity in the isolated perfused rat heart. *JMCC* 1981;13:741–752.

Langslet A, Oye I, Lie SO: Decreased cardiac toxicity of Adriamycin and daunorubicin when bound to DNA. *Acta Pharm. et Toxicol.* 1974;35:379–385.

Herman EH, Rahman A, Ferrans VH, Vick JA, Schein PS: Prevention of chronic doxorubicin cardiotoxicity in beagles by liposomal encapsulation. *CancerResearch* 1983;43:5427–5432.

Van Boxtel C, Olson RD, Boerth RC, Oates J: Doxorubicin inotropic effects and inhibitory action on ouabain. *J. Pharm. Exp. Ther.* 1978;207:277–283.

Somberg J, Cagin N, Levitt B, Bounous H, Ready P, Leonard D, Anagnostopoulos C: Blockade of tissue uptake of the antineoplastic agent, doxorubicin. *J. Pharm. Exp. Ther.* 1978;204:226–229.

Herman EH, Mhatre RM, Lee IP, Waravdekar VS: Prevention of the cardiotoxic effects of Adriamycin and daunomycin in the isolated dog heart. *Proc. Soc. Exp. Biol.* 1972;140:234–239.

Hu ST, Brandle E, Zbinden G: Inhibition of cardiotoxic, nephrotoxic and neurotoxic effects of doxorubicin by ICRF–1 59. *Pharmacology* 1983;26:210–220.

Herman EH, Mhatre RM, Chadwick DP: Modification of some of the toxic effects of daunomycin (NSC–82,151) by pretreatment with the antineoplastic agent ICRF 159 (NSC–129,943). *Toxicol. Appl. Pharm.* 1974;27(3):517–26.

Herman EH, Ferrans VJ: Influence of vitamin E and ICRF–187 on chronic doxorubicin cardiotoxicity in miniature swine. *Lab. Invest.* 1983;49(1):69–77.

Herman EH, Ferrans VJ, Myers CE, Van Vleet JF: Comparison of the effectiveness of (+/–)–1,2–bis(3,5–dioxopiperazinyl–1–yl)propane (ICRF–187) and N–acetylcysteine in preventing chronic doxorubicin cardiotoxicity in beagles. *Cancer Research* 1985;45(1):276–281.

Herman EH, el–Hage AN, Creighton AM, Witiak DT, Ferrans VJ: Comparison of the protective effect of ICRF–187 and structurally related analogues against acute daunorubicin toxicity in Syrian golden hamsters. *Res. Commun. Chem. Pathol. Pharm.* 1985;48(1):39–55.

Herman EH, Ferrans VJ, Young RS, Hamlin RL: Effect of pretreatment with ICRF–187 on the total cumulative dose of doxorubicin tolerated by beagle dogs. *Cancer Research* 1988;48(23):6918–6925.

Nemec J: Modification of Adriamycin cardiotoxicity by damvar. *Neoplasma* 1979;26(5):525–530.

Weitzman SA, Lorell B, Carey RW, Kaufman S, Stossel TP: Prospective study of tocopherol prophylaxis for anthracycline cardiac toxicity. *Curr. Ther. Res.* 1980;28(5):682–686.

Dresdale AR, Barr LH, Bonow RO, Mathisen DJ, Myers CE, Schwartz DE, d'Angelo T, Rosenberg SA: Prospective randomized study of the role of N–acetyl cysteine in reversing doxorubicin–induced cardiomyopathy. *Am. J. Clin. Oncol. (CCT)* 1982;5:657–663.

Myers CE, Bonow R, Sebastian P, Jenkins J, Corden B, Locker G, Doroshow J, Epstein S: A randomized controlled trial assessing the prevention of doxorubicin cardiomyopathy by N–acetylcystein. *Seminars in Oncology* 1983;10(1)1:53–60.

Lenzhofer R, Gatizinger U, Rameis H, Moser K: Acute cardiac toxicity in patients after doxorubicin treatment and the effect of combined tocopherol and nifedipine pretreatment. *J. Cancer Res. Clin. Oncol.* 1983; 1 06(2):143147.

Rabkin SW, Godin DV: Adriamycin cardiotoxicity and calcium entry blockers: the need for caution in the combination. *Can. J. Cardiol.* 1985; 1 (5):IV–VII.

Legha SS, Wang YM, Mackay B, Ewer M, Hortobagyi GN, Benjamin RS, Ali MK: Clinical and pharmacologic investigation of the effects of a–tocopherol on adriamycin cardiotoxicity. *Ann. N.Y. Acad. Sci.* 1982;393:411–418.

Villani F, Comazzi R, DiFronzo G, Bertuzzi A, Guindani A: Evaluation of doxorubicin cardiotoxicity in patients treated intermittently with 9–methyidigoxin. *Tumori* 1982;68(4):349–353.

Unverferth DV, Jagadeesh JM, Unverferth BJ, Magorien RD, Leier CV, Balcerzak SP: Attempt to prevent doxorubicin–induced acute human myocardial morphologic damage with acetyicystein. *J. Natl. Cancer Inst.* 1983;106(2):148–152.

Herman et al, Protection Against Acute Daunorubicin Toxicity . . . FASEB Absracts. Mar. 10, 1992, vol. 41, No. 5, p. 1477, Abstr. No. 7055.

Wadler et al. Synergistic Activity of Doxorubicin and The. . . Cancer Research. Mar. 1986, vol. 46, pp. 1176–1181.

Cancer Research, vol. 41, issued Sep. 1981, Herman et al, "Reduction of Chronic Doxorubicin Cardiotoxicity in Dogs. . . ", pp. 3436–33440.

Cancer Research, vol. 45, issued Jan. 1985, Herman et al, "Comparison of The Effectiveness of (±)–1,2–Bis (3.5–dioxopiperazinyl . . . ", pp. 276–281.

Research Communications in Chemical Pathology & Pharmacology, Herman et al., Reduction of Chronic Dauno–rubicin Cardiotoxicity By ICRF–187 in Rabbits, vol. 31, No. 1 (Jan., 1981).

FIG. 2

REDUCTION OF ANTHRACYCLINE-INDUCED CARDIOTOXICITY

This is a continuation of application Ser. No. 07/860,581, filed Mar. 27, 1992 now U.S. Pat. No. 5,242,901; which is a continuation of Ser. No. 07/702,741, filed Apr. 15, 1991, later abandoned; which is a continuation of Ser. No. 07/579,174, filed Sep. 5, 1990, later abandoned; which is a continuation of Ser. No. 07/149,114, filed Jan. 27, 1988, later abandoned.

The U.S. government has rights in this invention based upon research support in the form of Grant PHS 36524 from the public Health Service, Department of Health and Human Services.

FIELD OF THE INVENTION

The present invention relates to treatment of anthracycline-induced cardiotoxicity. More particularly, the invention is directed to the reduction of cardiotoxicity associated with anthracycline treatment by administration of (±)-1,2-bis(3,5-dioxopiperazinyl-1-yl)propane (bisdioxopiperazine).

BACKGROUND OF THE INVENTION

Anthracycline antineoplastics include doxorubicin (sold under the trademark ADRIAMYCIN, NSC 123127, from Adria Laboratories, Columbus, Ohio), an antibiotic isolated from the culture of a mutant *Streptomyces peucetius* strain. Other anthracyclines include: daunorubicin (sold under the trademark CERUBIDINE, from Wyeth Laboratories, Philadelphia, Pa.) epirubicin (4' epi-doxorubicin), THP-Adriamycin, and idarubicin (4' deoxy-doxorubicin).

Doxorubicin is effective as an anti-tumor agent against a variety of neoplasms. It is believed that doxorubicin's anti-tumor effects are due to DNA inhibition by intercalation between base pairs and/or steric inhibition of RNA activity.

Doxorubicin is effective in treatment of acute leukemias and malignant lymphomas. It is also very effective in the treatment of solid tumors, particularly when administered as part of a combination regimen. Thus, when used with cyclophosphamide, vincristine, bleomycin, and prednisone (BACOP), non-Hodgkin's lymphomas can be treated. Hodgkin's disease can be treated using a regimen of doxorubicin with bleomycin, vinblastine, and dacarbazine (ABVD). Carcinoma of the ovary is treated with a combination of cyclophosphamide, doxorubicin and cisplatin. Doxorubicin is effective against a number of sarcomas, e.g., osteogenic, Ewings's and soft-tissue sarcomas, and is considered the drug of choice, alone or in combination with other chemotherapeutic agents, in the treatment of metastatic adenocarcinoma of the breast, carcinoma of the bladder, bronchogenic carcinoma, neuroblastoma, and metastatic thyroid carcinoma. Doxorubicin has also shown activity in the treatment of carcinomas of the endometrium, testes, prostate, cervix, head and neck, and plasma-cell myeloma. Another widely used combination chemotherapy involves the use of doxorubicin, cyclophosphamide, and fluorouracil (FDC). FDC is used most commonly for the treatment of metastatic carcinoma of the breast.

The chief acute toxic effect of doxorubicin is myelosuppression. The peak of myelosuppression usually occurs at approximately 14±2 days, with recovery occurring at 15–18 days. Alopecia (hair loss) occurs frequently and begins in the third or fourth week of treatment. Nausea and vomiting occur regularly. Patients typically receive doxorubicin in dosages of 50–75 mg/m$^2$ (milligrams per square meter of body surface) per 21 day cycle.

Another important toxic effect of doxorubicin, and other anthracyclines, is cardiotoxicity. Patients who have received accumulated doxorubicin doses greater than 450 mg/m$^2$ are considered at high risk (greater than 10%) for the development cardiotoxicity, such as clinical heart failure. Cardiotoxicity is the major limitation in the usefulness of doxorubicin. In addition to clinical heart failure, cardiotoxicity encompasses clinical cardiotoxicity such as congestive heart failure and/or cardiac arrhythmias, and subclinical cardiotoxicity such as that detected by pathologic changes in cardiac biopsy or decrease in ventricular ejection fractions. Thus, it has been found that doxorubicin treatment often must be terminated before the maximum effective cumulative dose has been administered to a patient bearing a neoplasm, because of the development of life-threatening cardiomyopathy. Cardiotoxicity is manifested by chronic congestive heart failure, unresponsive to digitalis. At cumulative dosages of 300 mg/m$^2$ it has been demonstrated that about 50% of women with breast cancer develop a fall in the left ventricular ejection fraction (LVEF), measured by multi-gated radionuclide angiographic (MUGA) scan. Thus, although doxorubicin is considered a highly effective anti-tumor agent, this effectiveness is mitigated by the concomitant cardiotoxicity encountered with use of the drug.

The mechanism for doxorubicin (and other anthracycline)-induced cardiotoxicity is not completely understood, but is believed to involve drug-induced, cytotoxic, free-radical formation. These free radicals are formed via a cytochrome P450 reductase-mediated reaction and the formation of a semiquinone radical intermediate. As a result, damage occurs to mitochondrial membranes, endoplasmic reticulum, and nucleic acids. The heart muscle is particularly susceptible to free-radical damage because it has less protective superoxide dismutase and catalase activity than other tissues. Further, doxorubicin directly depresses cardiac glutathione peroxidase activity, the major defense against free-radical damage.

It has been found that doxorubicin binds with iron with high affinity. In vitro, the iron-doxorubicin complex causes oxygen radical formation and marked lipid peroxidation. The iron-doxorubicin complex has also been determined to cause increased oxygen radical production over doxorubicin alone.

If the cardiotoxicity associated with doxorubicin could be overcome, this drug, administered alone or in combination with other chemotherapeutic agents, would be the treatment of choice in many situations. For example, administration of doxorubicin is typically terminated when the total cumulative dose attains 450 mg/m$^2$, because it has been found that at this dosage approximately 5–10% of patients develop unacceptable clinical toxicity. In addition, many patients already receiving doxorubicin at this maximum dosage could derive substantial benefit from even higher dosages. However, increased dosages have been precluded by the increased risk of cardiotoxicity. The risk increases sharply with increasing cumulative dosages above 450 mg/m$^2$. For an even greater number of patients where doxorubicin would otherwise be part of the treatment of choice, the drug must be withheld completely because of high cardiac risk factors, e.g., age, chest-wall radiation from previous cancer treatment, or cardiac disease. This is particularly true when adjuvant ("preventive") chemotherapy is considered. For example, doxorubicin is sometimes used in an adjuvant setting. Patients with breast cancer are often treated by surgery for removal of the primary tumor sometimes followed by radiation therapy. In this situation, it is common to administer adjuvant chemotherapy following treatment of the primary tumor to prevent recurrence. Here, the risk of cardiotoxicity may outweigh the possible benefit of such preventive therapy. Adjuvant doxorubicin is also used in treatment of sarcomas, lymphomas, and leukaemia. In these cases, the risk of cardiotoxicity in otherwise apparently healthy patients (i.e., no longer suffering from primary tumor) may be too great to justify adjuvant chemotherapy with doxorubicin.

To reduce the occurrence of cardiotoxicity associated with doxorubicin administration, three strategies have been pursued. One method is to alter the dosing schedule of the drug. It is believed that the cardiotoxic effects of anthracyclines are related at least in part to peak blood levels of the drug, while anti-tumor activity is related to total drug exposure. Partial success in reducing cardiotoxicity while maintaining tumoricidal effects has been achieved by administering e.g., doxorubicin by infusion over extended periods, e.g., 96 hours. Although this method has produced a small but measurable decrease in cardiotoxicity, it requires patients to wear portable, but inconvenient, infusion devices, or indwelling catheters and pumps are necessary for prolonged infusions, causing long and expensive hospitalization. Altogether, infusion over extended periods is difficult in an out-patient setting.

A second approach to the reduction of cardiotoxicity of anthracyclines was an effort to develop anthracycline analogues having the anti-tumor activity of e.g., doxorubicin, without the cardiotoxicity. To date, no such analogues have been found which clearly meet these criteria.

A third strategy, the subject of this patent application, is the mitigation of anthracycline cardiotoxicity using cardioprotective agents. This approach is attractive because it allows well-established administration schedules of anthracyclines to be maintained without resort to prolonged infusions. This strategy presumes that separate mechanisms are responsible for tumoricidal and cardiotoxic effects of anthracyclines.

Studies have been conducted with several agents believed to be cardioprotective agents. Alpha-tocopherol and N-acetyl cysteine have been evaluated as cardioprotective agents only partially in mice, but studies in humans and other species, did not result in significant cardioprotection against doxorubicin-induced toxicity. Two agents which have shown promise as doxorubicin cardioprotectors in studies performed with non-cancer-bearing animals, are ICRF 159 and ICRF 187.

ICRF 159 (NSC 129943) and ICRF 187 (NSC 159780) are chelating agents of the bis(dioxopiperazine) family, chemically resemble ethylenediaminetetraacetic acid (EDTA), and have the formula (±)-(1,2-bis(3,5-dioxopiperazinyl-1-yl)propane. ICRF (Imperial Cancer Research Fund) 187 is the (+) enantiomer of ICRF 159 and is more water soluble. Thus, ICRF 187 is the preferred isomer for the preparation of parenteral injections.

ICRF 159 and 187 were initially investigated for antitumor activity. Unfortunately, both compounds were found to have little effect against human tumors when administered as single agents. Although the mechanism of action of bis(dioxopiperazine)s in reducing anthracycline cardiotoxicity is unknown, these compounds chemically resemble EDTA, and have potent chelating activity. ICRF 187 has been reported to form a bidentate chelator by intracellular hydrolysis. It has also been reported that EDTA can prevent erythrocyte ghost destruction by the iron-doxorubicin complex, possibly by chelating with bivalent iron. Thus it is believed by the present inventors, though it has not been demonstrated, that the chelating agent competes with doxorubicin for intracellular iron (and therefore prevents free radical formation), or that it may act as a free radical scavenger within the cardiac cell.

Several animal studies have been conducted to assess the cardioprotective effect of ICRF 187 when used in conjunction with an anthracycline. For example, an article by Herman, E. H. et al, in *Cancer Treat. Rep.* 63: 89–92, 1979, reported that a reduction of lethality and cardiotoxicity associated with administration of the anthracycline daunorubicin, was obtained by prior administration of ICRF 187 in non-cancer-bearing Syrian golden hamsters.

In 1981, Herman, E. H. et al, reported in *Res. Com. Chem. Path. Pharm.* 31: 85–97, that chronic daunorubicin cardiotoxicity was reduced by ICRF 187 administration in non-cancer-bearing rabbits. The ICRF 187 was administered 30 minutes prior to the daunorubicin at doses of 12.5 and 25 mg/kg (milligrams per kilogram of body weight).

An article published in *Cancer Res.* 41 3436–3440, 1981, by Herman, E. H. et al, showed a reduction in chronic cardiotoxicity induced by Adriamycin in normal (non-cancer-bearing) beagle dogs if administration of Adriamycin was preceded by administration of ICRF 187. In this randomized study, ICRF 187 administered at 12.5 mg/kg 30 minutes prior to injection with Adriamycin at 1.0 mg/kg, prevented cardiotoxicity in all treated animals.

Herman, E. H et al published a report in *Lab. Invest.* 49: 69–77, 1983, that doxorubicin treatment lead to myocardial lesions in eight of nine non-cancer-bearing miniature swine. However, cardiac lesions were absent in two, and minimal in five of the seven animals given doxorubicin (at 14.4 mg/kg) in combination with ICRF 187.

In another beagle study, Herman, E. H. et al reported, at *Cancer Res.* 45: 276–281, 1985, that no abnormalities were found in the hearts of three of six non-cancer-bearing dogs administered doxorubicin and ICRF 187, and that the remaining three dogs had minimal heart lesions.

In one human study of the toxic effect of ICRF 187 administered as an antitumor agent, it was found that dose limiting toxicity occurs at 1500 mg/m$^2$ administered three times daily, every three days, in patients with cancer. For this study, ICRF 187 was the only chemotherapeutic agent administered. At this dosage level the predominant adverse effects were leukopenia and thrombocytopenia. The cardiotoxic effects at this dosage included mild elevations of SGOT (serum glutamate-oxalate transaminase) and SGPT (serum glutamic-pyruvic transaminase), occasional vomiting and some alopecia (hair loss) (See, Von Hoff, D. D. et al, *Cancer Treat. Rep.* 65: 249–252, 1981).

SUMMARY OF THE INVENTION

It is highly desirable to exploit the full potential of anthracyclines, and other antitumor agents, by decreasing the risk of cardiotoxicity associated with use of anthracyclines without substantially affecting the anti-tumor activity of the anthracycline. The use of bis(dioxopiperazine)s was found to reduce the risk of cardiotoxicity with doxorubicin administration in non-cancer-bearing animals as early as 1981. However, it has now been unexpectedly discovered that bis(dioxopiperazine)s, when administered with anthracyclines and other anti-tumor drugs, has a cardioprotective effect in humans with cancer, and in some patients, more courses of chemotherapy will be tolerated than when a bis(dioxopiperazine), such as ICRF 187, is not administered. Unfortunately, for most patients with advanced breast cancer, the ability to tolerate a higher cumulative dose of doxorubicin does not result in a more effective treatment of the cancer. For some cancers, especially breast cancer, resistance is developed as cumulative dosages of anthracycline such as doxorubicin increase. The dosage at which resistance is developed is highly variable among a group of patients. For these patients the present invention has the advantage of reducing the incidence of cardiotoxicity associated with doxorubicin chemotherapy. For this reason, survival times for many cancer patients receiving treatment according to the present invention are not expected to significantly increase, but they will increase only to the extent that deaths are related to doxorubicin cardiotoxicity (i.e., not to the cancer). A small percentage of patients, approximately 10–25%, will continue to respond to increased dosages, and do not attain resistance to the tumoricidal effects of doxorubicin, although cardiotoxic effects are still present. For these patients, the present invention has the advantage of both reducing cardiotoxicity and increasing the anti-tumoricidal effect of doxorubicin.

The present invention also provides effective dosing schedules for humans. Dosing schedules for bisdioxopiperazine administered with anthracyclines such as doxorubicin in cancer-bearing patients were not previously known. Further, the present invention includes a combination of several antitumor drugs administered with doxorubicin to provide high anti-tumor efficacy, and reduced cardiotoxicity.

DETAILED DESCRIPTION OF THE INVENTION

The treatment of cancer by chemotherapy is dependent on several factors, including the type of cancer, the general health and age of the patient, and the stage of the cancer. Well known antitumor agents include 5-fluorouracil, cyclophosphamide and doxorubicin (Adriamycin). Often, an antitumor agent is administered in combination with other antitumor agents, and/or other anti-tumor regimens, such as radiation therapy and surgery. One well studied combination of drugs is 5-fluorouracil, doxorubicin, and cyclophosphamide, known as "FDC" (also known as "FAC" (Adriamycin)). FDC is useful in the treatment of mammary adenocarcinoma, although it is sometimes used to treat to lung cancer as well, especially small cell lung cancer. The cardioprotective effect of ICRF 187 is manifest when ICRF 187 is administered as part of a chemotherapy regimen including an anthracycline. The cardioprotective effect of ICRF 187 is independent of whether the patient has cancer or not.

Although cardioprotective effects of ICRF 187 were found when the drug was administered with anthracyclines in animals, such animal results are not necessarily predictive of the toxicity and efficacy of the drug combination in humans. It was therefore necessary to perform tests in humans suffering from cancer. A randomized clinical study was conducted with women suffering from advanced, inoperable and metastatic breast cancer. The study was conducted to determine whether ICRF 187 can prevent cumulative anthracycline-induced cardiotoxicity in humans.

Advanced metastatic breast cancer was chosen as a suitable cancer for study for several reasons. The chemotherapy treatment of choice for breast cancer is FDC. Thus, a group of patients could be chosen who could be treated with a uniform treatment regimen. Further, the rate and duration of response in these patients is sufficiently high to insure that an adequate number of patients would receive a high enough cumulative dosage of doxorubicin to make cardioprotection an important factor in their treatment.

The FDC chemotherapy regimen chosen for the study can be administered in several different dosage combinations and cycles of administration. Thus, doxorubicin (Adriamycin, Adria Laboratories, Columbus, Ohio), is generally administered in a dose of 50–90 $mg/m^2$ administered intravenously by slow IV push, the dosage repeated at 21 day intervals. An alternative dose schedule includes weekly doses of 20 $mg/m^2$, or 30 $mg/m^2$ given on each of three successive days repeated every four weeks. Doxorubicin can be administered either intravenously or (less frequently) intraarterially.

Cyclophosphamide (Cytoxan, Bristol-Myers Co., Syracuse, N.Y.), can be administered intravenously or intraarterially on a daily, twice weekly, weekly, or once every 21 day schedule, in dosage ranges of 100, 300, 600, and 500–1500 $mg/m^2$, respectively. In bone marrow transplant treatment up to 4000 $mg/m^2$ is administered intravenously. Cyclophosphamide can be administered orally in dosages of 50–200 mg/day for up to 14 days. The treatment can be repeated according to various schedules, e.g, every two weeks, or continuously.

Fluorouracil (Adrucil, Adria Laboratories, Columbus, Ohio), can be administered in a wide variety of dosage schedules. For example, the drug can be administered 500 $mg/m^2$ intravenously every 21 days; orally given 200 mg/kg/day; by intravenous infusion 10–20 mg/kg/day; or topically twice daily (EFUDEX creme, Roche Laboratories, Nutley, N.J.). Fluorouracil can be administered orally, however this route is usually not used due to very poor absorption.

The preferred FDC regimen is: Adriamycin, 50 $mg/m^2$ administered intravenously by slow IV push over 15 minutes; Cyclophosphamide 500 $mg/m^2$ administered intravenously; and fluorouracil, 500 $mg/m^2$ administered intravenously. The FDC regimen is preferably administered once every 21 days.

As discussed below, dose modification must be made in the regimen for each patient as treatment progresses, primarily to alleviate toxic side effects from the drugs.

ICRF 187 used in the study was obtained from the National Cancer Institute, Bethesda, Md. ICRF 187 can be administered at doses of between 500 and 4500 $mg/m^2$, over 1–3 days, repeatable every three weeks, and administered by intravenous infusion or bolus. Administration can also be made by 24 hour infusion given once a week, or intravenous bolus for three consecutive days repeated every three weeks. The preferred dose is 1000 $mg/m^2$ administered intravenously over 15 minutes, 30 minutes prior to initiation of FDC administration.

ICRF 159 cannot be administered intravenously because of its low solubility. It is therefore, administered orally. The dose limiting toxicity of ICRF 187 occurs at 1500 $mg/m^2$ administered daily, for three consecutive days every three weeks.

Due to the flexibility of administration schedules for both ICRF 187 and ICRF 159, it is possible to administer these agents in conjunction with anthracyclines as part of a chemotherapy regimen which includes an anthracycline.

The essential consideration in determining when to administer ICRF 187 relative to an anthracycline, is the bioavailability of ICRF 187 in a cardioprotective amount, during administration of a cardiotoxic anthracycline such as doxorubicin. It is believed that ICRF 187 can be administered between about one hour prior to FDC administration and about one hour after FDC administration. Preferably, the ICRF 187 should be administered between about 30 minutes before and simultaneously with FDC administration. Most preferably, ICRF 187 is administered 30 minutes before FDC administration. Other schedules for the relative administration of ICRF 187 or ICRF 159 and anthracyclines, can be readily determined based on the above discussion, by routine experimentation. The subject invention provides a biologically effective human anti-neoplastic composition including in combination: an anthracycline; and a cardioprotective amount of (+)-1,2-bis(3,5-dioxopiperazinyl-1-yl)propane. In one embodiment, the invention provides such a biologically effective human anti-neoplastic composition wherein the anthracycline is doxorubicin. In another embodiment doxorubicin in this composition is administered in conjuction with fluorouracil and cyclophosphamide. The subject invention also provides a biologically effective human anti-neoplastic composition, including in combination: an anthracycline; and (+)-1,2-bis(3,5-dioxopiperazinyl-1-yl)propane, the combination formulated such that after administration of the combination, a cardioprotective amount of (+)-1,2-bis(3,5-dioxopiperazinyl-1-yl) propane becomes bioavailable before an effective amount of the anthracycline becomes available. In one embodiment, the invention provides such a biologically effective human anti-neoplastic composition wherein said anthracycline is doxorubicin. In another embodiment doxorubicin in this composition is administered in conjuction with fluorouracil and cyclophosphamide. In addition, the invention provides this composition wherein (+)-1,2-bis(3,5-dioxopiperazinyl-1-yl)propane is administered at a dosage of between 500 and 4500 mg/m$^2$. In a further embodiment, (+)-1,2-bis(3,5-dioxopiperazinyl-1-yl)propane is administered at a dosage of 1000 mg/m$^2$. In yet another embodiment, (+)-1,2-bis(3, 5-dioxopiperazinyl-1-yl)propane and the anthracycline are administered at a ratio of between 10 to 1 and 30 to 1.

The following examples illustrate the study protocol, including patient selection criteria, randomization and stratification, therapy, cardiac evaluation, anti-tumor evaluation, non-cardiotoxicity, and patient withdrawal.

EXAMPLE I (Patient Selection Criteria)

All patients considered for inclusion in the study had histologically proven, advanced or metastatic carcinoma of the breast. To be eligible, a patient must have recovered from any side effects encountered with previous therapies. Previous therapies could not have included treatment with doxorubicin or other anthracyclines. Prior adjuvant chemotherapy was acceptable if a recurrence was found six months after the cessation of therapy.

A history of prior antineoplastic hormonal therapy with agents such as megestrol acetate, tamoxifen citrate, diethylstilboestrol, medroxyprogesterone acetate or fluoxymesterone, was not a disqualifying factor for participation, provided the patient had been withdrawn from such therapy for at least the previous two weeks with progressive disease or had rapidly progressed while receiving hormones.

Patients with prior radiotherapy were eligible if (1) radiation had been completed at least two weeks previous to consideration for inclusion, (2) the radiation did not include greater than 50% of the pelvic bone structure, and (3) there had been evaluable or measurable disease outside of the field of radiation.

Patients were required to have an adequate performance status (ECOG 0, 1, 2, 3), (ECOG is a qualitative scale of relative performance status defined by the Eastern Cooperative Oncology Group—based on a scale of 0–4. An ECOG of 0 indicates full ambulatory performance with no symptoms; an ECOG of 4 indicates a bed ridden patient with no capacity for normal activity); bone marrow function (white blood cell count greater than 4,000/mm$^3$; platelet count of greater than 100,000/mm$^3$; renal function (creatinine less than or equal to 2 mg/dl) and hepatic function (total bilirubin less than 3 mg/dl and SGOT less than 60 u/l, except when the liver was found to be the site of metastatic disease).

Patients could not be included if active cardiac disease were found. Baseline LVEF (left ventricular ejection fraction) had to be greater than 0.45.

Patients were excluded from the study if (1) the above criteria were not met; (2) history of other malignancy was found (other than "cured" cervical cancer and curatively treated basal cell or squamous cell skin cancer); (3) myocardial infarction within the prior 12 months had occurred; (4) active angina pectoris was present; (5) symptomatic valvular heart disease was present; (6) uncontrolled congestive heart failure was present; and (7) other uncontrolled medical or psychiatric problems had occurred.

By the above criteria, 92 patients were entered on the study. Informed consent was obtained for each patient.

EXAMPLE II (Stratification and Randomization)

Patients selected for study were stratified prior to randomization. Stratification was based on prior adjuvant chemotherapy ("yes" or "no") and cardiac risk factors ("yes" or "no"). Cardiac risk is defined as (1) age greater than 65; (2) prior radiation to the heart, mediastinum or chest wall; (3) history of hypertension (blood pressure of 140/90 or higher), cardiac failure, diabetes mellitus, prior infarction within 12 months, angina, rheumatic heart disease or and abnormal EKG. Patients were randomized to receive a standard regimen of fluorouracil, cyclophosphamide, and doxorubicin (FDC) alone, or the same FDC regimen plus ICRF 187. Randomization was done by a computer random number generator for each stratified category.

Forty-five patients were placed in the FDC arm of the study, and forty-seven patients were placed in the FDC+ ICRF 187 arm. The treatment arms were balanced in terms of age, performance status, prior adjuvant chemotherapy, prior radiation therapy, prior hormonal therapy and preexistent cardiac disease, as shown in Table 1.

TABLE 1

| Patient Characteristics | | |
|---|---|---|
| | FDC | FDC + ICRF 187 |
| Number of Patients Accrued | 45 | 47 |
| Still On Study | 6 (13%) | 12 (26%) |

TABLE 1-continued

| Patient Characteristics | FDC | FDC + ICRF 187 |
|---|---|---|
| Age (Years) | | |
| Median | 57.0 | 58.3 |
| Range | 29–71 | 32–76 |
| Performance Status | | |
| 0 | 20 (44%) | 15 32%) |
| 1 | 13 (29%) | 18 (38%) |
| 2 | 11 (24%) | 14 (30%) |
| 3 | 1 (2%) | 0 |
| Previous Adjuvant Chemotherapy | 14 (31%) | 14 (31%) |
| Previous Hormonotherapy | 22 (49%) | 21 (45%) |
| Previous Radiotherapy | 7 (16%) | 11 (23%) |
| Cardiac Risk Factors | 26 (58%) | 29 (62%) |

EXAMPLE III (Therapy)

As discussed above, the FDC regimen included: doxorubicin (Adriamycin) 50 mg/m$^2$ administered intravenously by slow IV push; cyclophosphamide, 500 mg/m$^2$ administered intravenously; and fluorouracil, 500 mg/m$^2$ administered intravenously. Patients randomized to receive FDC+ICRF 187 were given the above regimen plus 1000 mg/m$^2$ ICRF 187 administered intravenously over 15 minutes, 30 minutes prior to initiation of FDC administration.

The therapy cycle was repeated every 21 days, subject to patient tolerance. Dosage reductions were made during the first two cycles based on nadir WBC and platelet counts, but only for fluorouracil or cyclophosphamide, in order that the doxorubicin dosage could be maintained at a constant level. No dosage modifications were made for ICRF 187.

Of the 92 patients entered in the study, 74 are now off study. The treatment received by these patients is tabulated in Table 2.

TABLE 2

Treatment Received by Patients Now Off Study

| | FDC | FDC + ICRF 187 |
|---|---|---|
| Number of Patients | 39 | 35 |
| Number of Treatment Cycles | | |
| Mean | 8.6 | 9.6 |
| Median | 8.9 | 9.3 |
| Range | 1–16 | 1–20 |
| Dose of Doxorubicin (mg/m$^2$) | | |
| Mean | 397.2 | 466.3 |
| Median | 448.3 | 450.3 |
| Range | 50–650 | 50–1000 |
| Cumulative Dose of Doxorubicin (mg/m$^2$) | | |
| 300 | 9 (23%) | 10 (29%) |
| 300–399 | 3 (8%) | 6 (17%) |
| 400–499 | 17 (44%) | 2 (6%) |
| 500–599 | 9 (23%) | 6 (17%) |
| 600–699 | 1 (3%) | 1 (3%) |
| 700–799 | 0 | 6 (17%) |
| 800–999 | 0 | 4 (11%) |

The modifications were made as follows: if the day one WBC count was less than 4000 mm$^3$ or platelet count was less than 100,000 mm$^3$, treatment was delayed for one week. If the nadir WBC was less than 1500 mm$^3$ and platelet count was between 75–100,000 mm$^3$, the fluorouracil and cyclophosphamide dosage was reduced to 75%. If the nadir WBC count was less than 1500 mm$^3$ or the granulocyte count was less than 1000 mm$^3$ and the platelet count was less than 75,000 mm$^3$, the fluorouracil and cyclophosphamide dosage was reduced to 50%. If the low nadirs persisted after reductions were made in the first two cycles, then the doxorubicin dosage was reduced using the same schedule as for the fluorouracil and cyclophosphamide dosages.

If the total bilirubin was greater than or equal to 2 mg/dl or the SGOT was between 60–150 u/l, the doxorubicin dosage was reduced by 50%. If the total bilirubin was between 2 and 3 mg/dl, and the SGOT was greater than 150 u/l, the doxorubicin dosage was reduced by 75%. If the WBC nadir was found to be greater than 1500 mm$^3$ after a cycle of dose reduction for hepatic function, the doxorubicin was increased to full dosage.

For stomatitis of ECOG Grade 2, the fluorouracil, doxorubicin and cyclophosphamide were each reduced in dosage by 25%. For stomatitis of ECOG Grade 3, the dosage of all three drugs was reduced by 50%.

Protocol-required dose modifications resulted in a mean of 90% of the projected fluorouracil and cyclophosphamide being received by patients in the FDC arm and 82% in the FDC+ICRF arm (p=0.05).

EXAMPLE IV (Cardiac Evaluation)

Because the dosage levels of doxorubicin administered during the study were expected to exceed cardiotoxicity thresholds, it was very important to closely monitor cardiac function, both before initiation of therapy, and at designated intervals during the study.

At the start of therapy all patients were given physical examinations, and medical histories were taken. An electrocardiogram, multigated radionuclide angiographic (MUGA) scan at rest and (when possible) with exercise, were made, and a chest x-ray was taken. These measurements were repeated at designated intervals throughout the treatment period.

Cardiologists, nuclear medicine physicians, and the pathologist involved in the study, were blinded to each patient's treatment group. The patient (and his oncologist) was aware of his treatment group.

Cardiac evaluations were made clinically by physical examination prior to each course of therapy, and at the time the patient went off-study. Each patient had a MUGA scan performed at baseline. Follow up cardiac scans were obtained at cumulative doxorubicin doses of 300 mg/m$^2$, 450 mg/m$^2$, and each 100 mg/m$^2$ thereafter. Resting equilibrium gated blood pool studies were performed using 20–30 mCi of $^{99m}$Tc-labeled red blood cells using an "in vivo" method: 1 mg of stannous chloride was injected intravenously, followed 20 minutes later by $^{99m}$Tc-pertechnetate. The gamma camera acquisition was gated over a sixteen frame interval in the left anterior oblique (LAO) and right anterior oblique (RAO) projections until a count density of approximately 250 counts/pixel were attained over the left ventricle. LAO gated radionuclide cardiac scans were performed with exercise when possible. Graded exercise at increments of 50 watts every 3 minutes was performed on a bicycle ergometer with the patient in a semi-erect position. Exercise imaging was performed for a minimum of three minutes.

Resting and exercise left ventricular ejection fractions were calculated from the LAO views using background-subtracted end-diastolic and the end-systolic frames. Regions of interest were drawn manually by an experienced nuclear physician. Segmental wall motion was assessed qualitatively from both the RAO and the LAO views. Ten percent of all MUGA scans were recycled "blindly" to the study cardiologist to assess consistency.

When each patient reached a cumulative doxorubicin dose of 450 mg/m$^2$ (or, when possible, when the patient went off study for disease progression or cardiac toxicity) an endomyocardial biopsy was performed to obtain samples of the right ventricular septum. The biopsy was performed via an internal jugular or femoral route. A right heart catheterization was performed using a triple linear thermodilution catheter. A No. 9 French right ventricular Stanford biotome was used. Position was confirmed fluoroscopically and five biopsies of the right ventricular septum were obtained. The biopsies were immediately placed in glutaraldehyde. Histologic sections were prepared and stained with hematoxylin-eosin. Tissue was also prepared for electron microscopy. Doxorubicin-induced changes were scored according to the Billingham scale (see Billingham et al, *Cancer Treat. Rep.*, 62: 865–872, 1978). The biopsy score was obtained from the average of the five samples taken. Right atrial and ventricular pressure and assessment of wall motion were also noted at the time of the cardiac biopsy.

There were 11 episodes of clinical cardiac toxicity in the FDC arm and 2 episodes in the FDC+ICRF 187 arm (p=0.02). These episodes were graded mild (Grade 1), moderate (Grade 2) and severe (Grade 3). Grade 1 included patients with either subjective (new exertional dyspnea in the absence of significant pulmonary disease or anemia) or objective signs (S3 gallop and/or rales) of congestive heart failure but who required no medication. Grade 2 included patients who needed medication to control congestive heart failure. Grade 3 included patients who needed hospitalization for treatment of severe heart failure.

In the FDC+ICRF 187 group there were only two Grade 2 patients. In the FDC arm there were three Grade 1, three Grade 2, and five Grade 3 patients.

Figure 1:
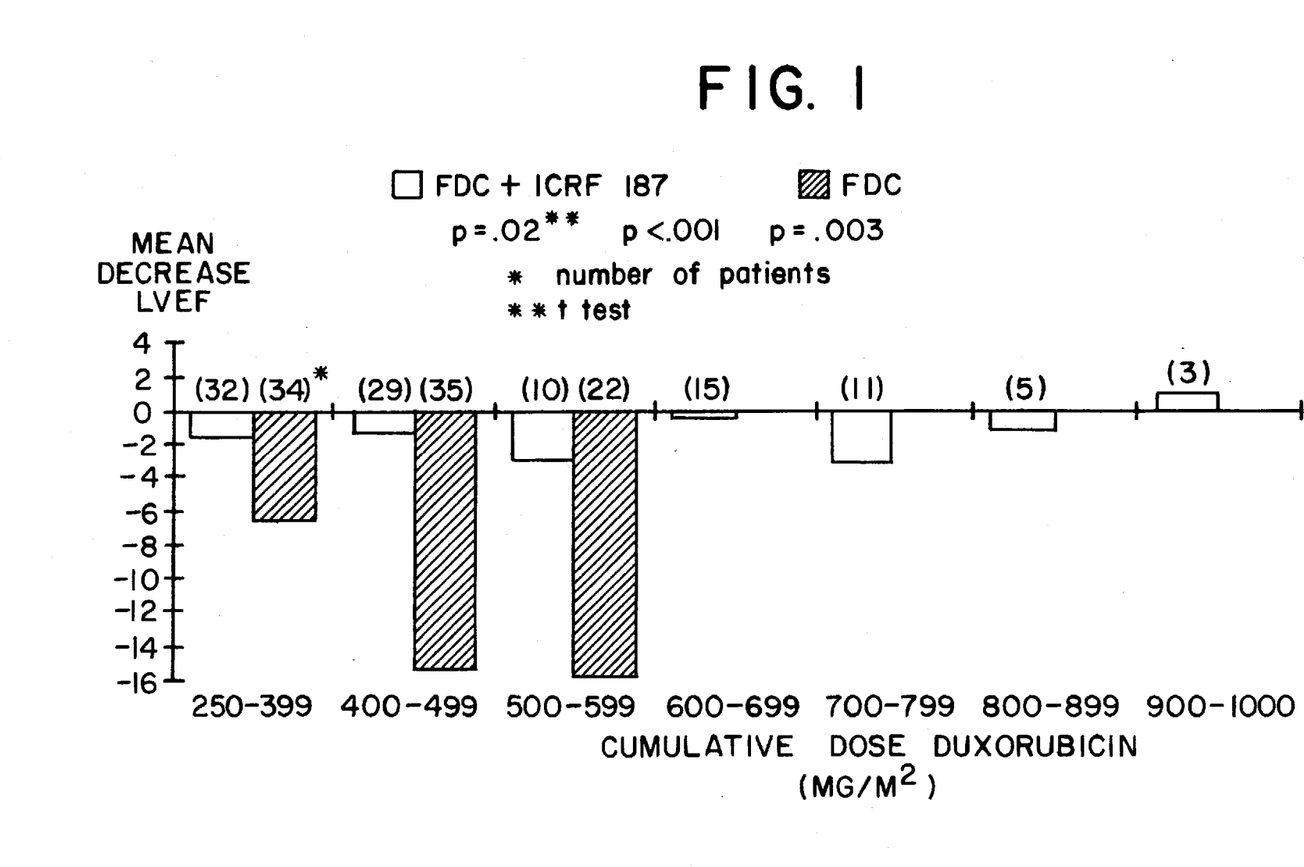
FIG. 1 is a chart showing the mean fall in resting left ventricular ejection fraction from baseline for various treatment groups at designated cumulative doses of doxorubicin.
Figure 2:
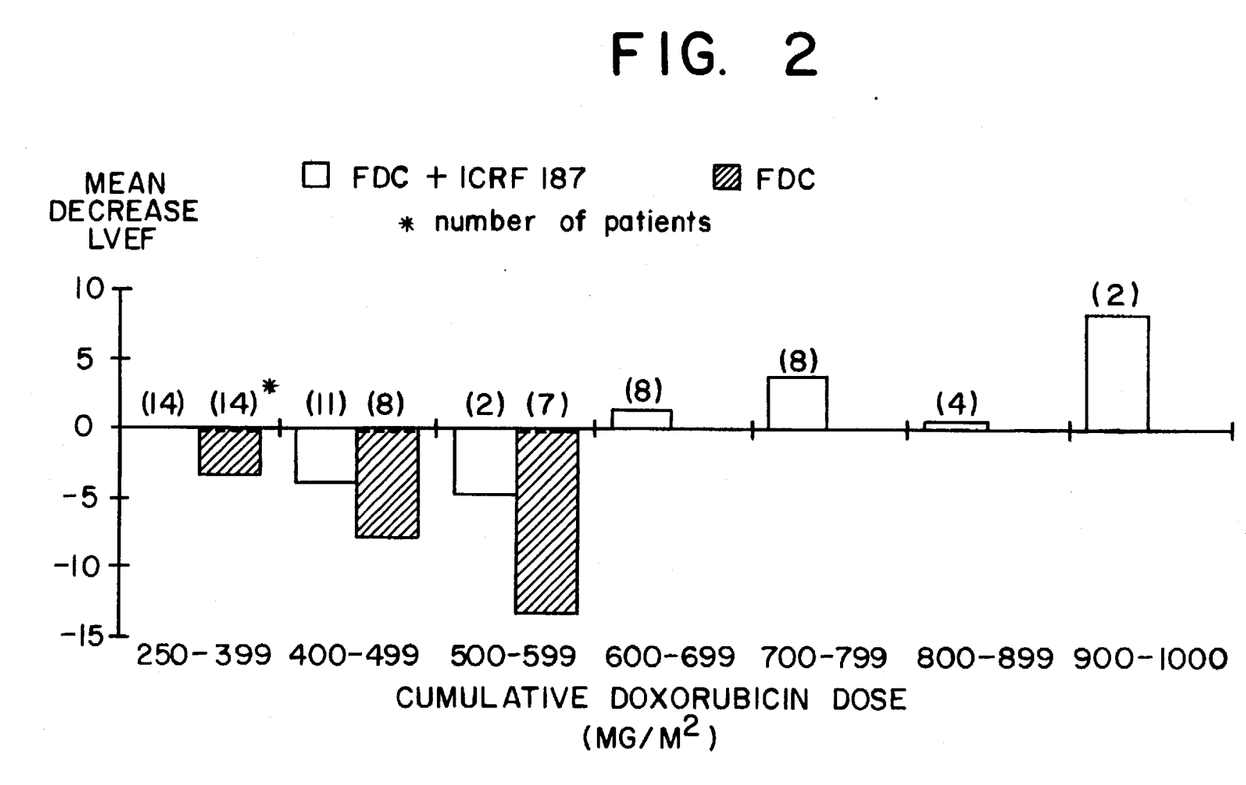
FIG. 2 is a chart showing the mean fall in exercise left ventricular ejection fraction from baseline for various treatment groups at designated cumulative doses of doxorubicin.

Assessment of cardiac toxicity by MUGA scan is shown in FIGS. 1 and 2. Changes in resting LVEF as measured by MUGA scan are expressed using changes from the baseline value for each patient who has completed treatment. FIG. 1 shows the mean fall in resting LVEF from baseline for each treatment group at designated cumulative doses of doxorubicin. FIG. 2 shows the mean fall in exercise LVEF from baseline.

The mean fall from baseline is significantly less for the FDC+ICRF 187 arm than the control arm at doxorubicin doses of 250–399 mg/m$^2$ (p=0.03); 400–499 mg/m$^2$ (p<0.001) and 500–599 mg/m$^2$ (p=0.003). At dose levels greater than 600 mg/m$^2$ only one patient on the FDC arm remained on study, compared to 11 patients on the FDC+ICRF 187 regimen. No apparent decrease in LVEF was found for these patients.

Measurement of cardiac toxicity by endomyocardial biopsy was performed for 26 patients: 13 for each arm of the study. These represent 52% of the FDC patients and 48% of the FDC+ICRF 187 patients who reached a cumulative doxorubicin dose of 450 mg/m$^2$. One biopsy in the FDC arm and 2 in the FDC+ICRF 187 arm were done at 550 mg/m$^2$.

The biopsy scores are shown in Table 3:

TABLE 3

Endomyocardial Biopsy Results

| SCORE | FDC | FDC + ICRF 187 |
|---|---|---|
| 0.0 | 3 | 7 |
| 0.5 | 1 | 0 |
| 1.0 | 2 | 6 |
| 2.0 | 5 | 0 |
| Unevaluable | 3 | 0 |
| Total | 13 | 13 |
| Mean | 1.14 | 0.46 |

The difference in mean biopsy score of 1.14 versus 0.46 is statistically significant (p=0.03).

EXAMPLE V (Anti-tumor Evaluation)

At initiation of therapy each patient was assessed for baseline tumor; if possible, bi-dimensional measurements were obtained. X-rays and scans for assessment of tumor were performed at least every three cycles. Prior to each cycle, patients were evaluated with a physical exam which included performance status and weight.

Standard ECOG criteria for measurement of response were used. The complete disappearance of all tumor and normalization of scans and laboratory values for at least 30 days was considered a complete response. A partial response occurred if a greater than 50% decrease was found in the product of the perpendicular measurement of the largest diameters of all tumor nodules for at least 30 days, or bone lesions demonstrated healing on x-ray. For patients with evaluable disease in bone only, "improvement" was measured as a clear increase in performance status by at least one grade or to grade 0, or a decrease in analgesic requirements. Bone lesions must have remained stable for 8 weeks or longer.

The antitumor efficacy was similar for the regimen in each treatment arm, as shown in Table 4. The median time to progression of disease was 9.3 months for FDC patients, and 10.3 months for FDC+ICRF 187 patients (not significant).

TABLE 4

Antitumor Effect

|  | FDC | FDC + ICRF 187 |
|---|---|---|
| Patients Accrued | 45 | 47 |
| Not Evaluable | 1 | 3 |
| Complete Remission | 3 (7%) | 4 (9%) |
| Partial Remission | 17 (39%) | 17 (39%) |
| Stable | 24 | 21 |
| Immediate Progression (within one cycle) |  | 2 |
| Median Time to Progression | 9.3 months | 10.3 months |

Figure 3:
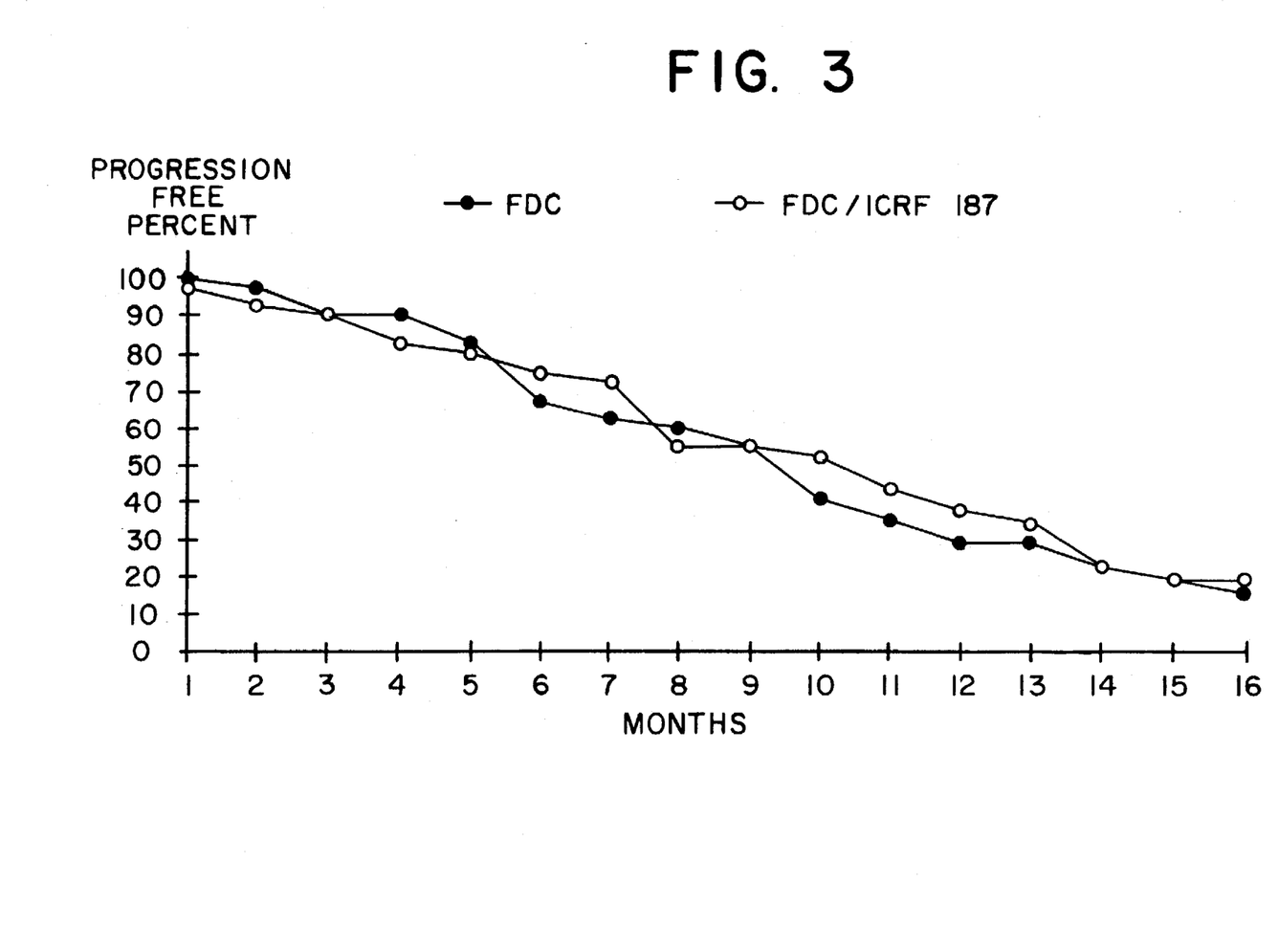
FIG. 3 is a graph showing time to progression of disease measured by percent of patients remaining progression-free versus time for patients treated with FDC and for patients treated with FDC+ICRF 187.

This data is shown graphically in FIG. 3. FIG. 3 shows time to progression measured by percent of patients progression-free over time. It can be seen that a cardioprotective effect is obtained without substantially affecting anti-tumor activity.

EXAMPLE VI (Non-cardiac Toxicity)

Prior to each therapy cycle, and at baseline, history and physical examination were taken for each patient. Complete blood counts were obtained prior to each cycle. During at least the first two cycles weekly complete blood counts were obtained. Serum chemistries were obtained with every other cycle.

It was determined that most measures of non-cardiac toxicity did not differ significantly between the two treatment groups. The incidence of mucositis, infection, fever with neutropenia, alopecia, nausea and vomiting were similar in the two arms. There were four treatment related deaths in the FDC arm. These included one patient with a cardiac death, two septic deaths and one infection without positive blood culture. There were two treatment related deaths in the FDC+ICRF 187 arm. These included one intracerebral hemorrhage and one septic death.

TABLE 5

Non-caridac Toxicity

|  | FDC | FDC + ICRF 187 |
|---|---|---|
| Patients Evaluable | 45 | 47 |
| Fever + Neutropenia | 5 | 5 |
| Infection | 4 | 6 |
| Toxic Death | 4 | 2 |
| Alopecia Grade 2 | 44 | 43 |
| Nausea + Vomiting (ECOG 2 + 3) | 30 | 30 |
| Stomatitis (ECOG 2 + 3) | 11 | 10 |

EXAMPLE VII (Removal From Study)

There was no predetermined cumulative dose for stopping administration of doxorubicin. Treatment was continued until the development of disease progression or toxicity. Patients were removed from the study if unacceptable (ECOG Grade IV) non-cardiac toxicity developed that could not be improved by dose modification. Cardiac criteria for removal from study included: (1) development of clinical signs of congestive heart failure; (2) a fall in the resting LVEF to less than 0.45 or a fall from baseline resting LVEF of greater than or equal to 0.20; or (3) endomyocardial biopsy rating of greater than or equal to a Billingham Grade 2.

As shown in Table 6, a total of 32 patients in the FDC arm were removed from study, and 25 patients were removed from study in the FDC+ICRF 187 arm.

TABLE 6

Reasons for Removal from Study

|  | FDC | FDC + ICRF 187 |
|---|---|---|
| Cardiotoxicity Alone | 15 | 4 |
| Cardiotoxicity + Other | 7 | 0 |
| Any Cardiotoxicity | 22 | 4 |
| Progression Alone | 10 | 21 |

The experiments set forth above indicate that doxorubicin-induced cardiotoxicity can be safely prevented with ICRF 187, a bisdioxopiperazine, and that patients who respond to doxorubicin-containing regimens may receive higher dose of this drug, then possible without ICRF 187. Use of the drug may be extended to patients previously precluded from doxorubicin treatment, such as those previously treated and patients with cardiac risk factors (such as radiation or advanced age) or in the adjuvant setting. Thus, of the patients in the study discussed above, 16% of the patients who received the FDC+ICRF 187 regimen were removed from treatment due to cardiac toxicity. For patients receiving FDC alone, 69% were removed for cardiac toxicity, and 43% were removed for cardiac toxicity alone. Therefore, it can be said that between 27 and 53% of the patients receiving FDC+ICRF 187 were saved from developing a cardiac toxic event.

What is claimed is:

1. A biologically effective human anti-neoplastic composition, comprising in admixture:

an anthracycline; and a cardioprotective amount of (+)-1,2-bis(3,5-dioxopiperazinyl-1-yl)propane.

2. The composition of claim 1 wherein said anthracycline is doxorubicin.

3. A biologically effective human anti-neoplastic composition comprising in admixture:

an anthracycline; and (+)-1,2-bis(3,5-dioxopiperazinyl-1-yl)propane, said composition formulated such that after administration of said composition, a cardioprotective amount of said (+)-1,2-bis(3,5-dioxopiperazinyl-1-yl)propane becomes bioavailable before an effective amount of said anthracycline becomes bioavailable.

4. The composition of claim 3 wherein said anthracycline is doxorubicin.

5. A pharmaceutical dosage form comprising a biologically effective human anti-neoplastic composition, wherein said composition comprises:

an anthracycline in admixture with a cardioprotective amount of (+)-1,2-bis(3,5-dioxopiperazinyl-1-yl)propane.

6. The pharmaceutical dosage form according to claim 5, wherein said dosage form is a solution suitable for intravenous administration.

7. The pharmaceutical dosage form according to claim 5, wherein said composition is formulated such that after administration of said composition a cardioprotective amount of said (+)-1,2-bis(3,5-dioxopiperazinyl-1-yl) propane becomes bioavailable before an effective amount of said anthracycline becomes bioavailable.

8. The pharmaceutical dosage form according to claim 7, wherein said dosage form is a solution suitable for intravenous administration.

* * * * *